United States Patent [19]

Kosaka

[11] Patent Number: 5,047,963
[45] Date of Patent: Sep. 10, 1991

[54] PARTICLE ANALYZING APPARATUS AND METHOD FOR DETERMINING NUCLEAR SHIFT INDEX

[75] Inventor: Tokihiro Kosaka, Hyogo, Japan

[73] Assignee: TOA Medical Electronics Co., Ltd., Kobe, Japan

[21] Appl. No.: 401,983

[22] Filed: Sep. 1, 1989

[30] Foreign Application Priority Data

Sep. 30, 1988 [JP] Japan .................. 63-246539

[51] Int. Cl.$^5$ ...................... G06F 15/42; G01N 15/02
[52] U.S. Cl. .................................. 364/555; 356/336; 356/339
[58] Field of Search ........................ 364/555, 497, 498; 73/865.5; 250/574; 356/336, 338, 339

[56] References Cited

U.S. PATENT DOCUMENTS

| | | | |
|---|---|---|---|
| 4,176,953 | 12/1979 | Bartoov et al. | 356/73 |
| 4,596,464 | 6/1986 | Hoffman et al. | 364/555 |
| 4,661,913 | 4/1987 | Wu et al. | 364/555 |
| 4,706,207 | 11/1987 | Hennessy et al. | 364/555 |
| 4,732,479 | 3/1988 | Tanaka et al. | 356/336 |
| 4,735,504 | 4/1988 | Tycko | 356/343 |
| 4,827,144 | 5/1989 | Zaitsu et al. | 250/574 |
| 4,830,494 | 5/1989 | Ishikawa et al. | 250/574 |
| 4,987,539 | 1/1991 | Moore et al. | 364/555 |

FOREIGN PATENT DOCUMENTS 0046643 3/1982 European Pat. Off. .
0268766 1/1988 European Pat. Off. .

OTHER PUBLICATIONS

An Article from Review of Scientific Instruments, vol. 55, No. 9 dated Sep., 1984, pp. 1375-1400 entitled, "Flow Cytometry".
An Article entitled, "Applications of Flow Cytometry in Clinical Diagnosis", from TRAC: Trends in Analytical Chemistry, vol. 3, No. 4, published 4/1984.
Article from the Journal of Histochemistry and Cytochemistry, vol. 27, pp. 321-324, published 1979 entitled, "A Multidimensional Slit-Scan Flow System".

Primary Examiner—Parshotam S. Lall
Assistant Examiner—Michael Zanelli
Attorney, Agent, or Firm—Fitch, Even, Tabin & Flannery

[57] ABSTRACT

A particle suspension is irradiated with a laser beam, and side-scattered light from a single particle irradiated in an irradiating zone is detected as one or a plurality of particle signals. The degree of complexity of the particle nucleus is determined by extracting high-frequency signal components contained in the particle signal, and the degree of symmetry of the particle nucleus is determined by extracting the magnitude of a difference between this single particle signal and a signal obtained by flipping over the particle signal in terms of time. The degrees of complexity and symmetry of the particle nucleus serve as data for particle analysis.

5 Claims, 7 Drawing Sheets

PARTICLE ANALYZING APPARATUS AND METHOD FOR DETERMINING NUCLEAR SHIFT INDEX

BACKGROUND OF THE INVENTION

1. Field of the Invention

This invention relates to a particle analyzing apparatus and method for measuring the nuclear shift index of particles by suitably preparing a liquid specimen such as blood, passing particles such as white blood cells contained in the specimen through a detecting zone to detect signals corresponding to the particles, and processing the detected signals.

2. Description of the Prior Art

White blood cells present in human blood are classified into monocytes, neutrophils, eosinophiles and basophils, and determining the numbers of particles according to class or the content of these particles as a percentage is a useful tool in clinical examination. Accordingly, in order to classify white blood cells into the aforementioned particles and enumerate the same automatically, apparatus heretofore developed for this purpose are adapted to dilute blood with a diluent, supply the diluted blood to a detector to detect any electrical or optical change produced when the blood cells pass through the detector, classify the particles and count the same.

A first conventional apparatus of this kind is adapted to destroy red blood cells by using a hemolytic agent to obtain an electrolyte in which only white blood cells are suspended, pass the electrolyte through a detector provided with pores, and detect a change in electrical impedance (e.g., electrical resistance) at the porous portion, the change occurring when white blood cells pass through the pores. This apparatus enables white blood cells to be identified based on a difference in the magnitude of the detected signal.

A second conventional apparatus is adapted to pass a dilute solution of blood, which is in the form of a fine stream, through the central portion of a flow cell, and irradiate the fine stream with light to detect an optical change, such as a change in fluorescence or scattered light, produced when the blood flows through the cell. With this apparatus, white blood cells can be identified based on a difference in fluorescent intensity or intensity of scattered light detected by staining the white blood cells.

The porous portion constituting the detecting section of the first conventional apparatus covers an area that is considerably large in comparison with particle size. For this reason, particles cannot be detected on a microscopic scale. By way of example, if particles having a diameter of several microns are to be detected, the pores would have to possess a hole diameter and pass length on the order of tens of microns to 100 microns in order to prevent clogging. In addition, the only information acquired relates to particle size.

With the second conventional apparatus, the detecting zone can be made smaller than the size of the particles by narrowing down the irradiating light flux. By this reducing of the size of the detecting zone, particles can be detected on a microscopic scale. In other words, various characteristics possessed by the particles can be detected in greater detail, so that a greater amount of information can be extracted.

For example, as set forth in the "Bulletin of the Electrotechnical Laboratory" by Yoshio Nomura, Vol. 44, No. 3, pp 185-186, and in "Flow Cytometry and Sorting" by L. L. Wheeless, et al., pp. 125-135, an apparatus is available in which irradiation is performed using a slit-shaped laser beam. Specifically, as shown in FIG. 10, a slit-shaped laser beam 124 having a width of approximately 4 $\mu$m is projected in a direction perpendicular to that of cell flow, and fluorescent profile is measured when the cells cross the laser beam 124. The detection signal thus obtained is illustrated in FIG. 11. Signal widths C and N are commensurate with the diameters of cell 120 and nucleus 122. Accordingly, the ratio of nuclear diameter to cell diameter is obtained from N/C. Using the slit beam also makes it possible to take measurements to determine whether polynuclear cells are present.

Further, in "Cytometry" by L. L. Wheeless, et al., Vol. 5, pp. 1-8, an example is described in which detection error ascribable to cell orientation is prevented. To this end, an X-Y-Z slit scanning method is used in which X and Y axes are taken in a plane containing the slit beam, and the direction of cell flow is taken as the Z axis with the fluorescent profile being analyzed in the X, Y and Z directions. Both parameters, namely the N/C ratio and nuclear fluorescent intensity obtained, are used to enable cell discrimination.

A problem encountered with the first conventional apparatus is that only particle size information can be obtained, as mentioned earlier. Therefore, in order to classify and quantify white blood cells, it is required that the group of white blood cells in each class be made large enough to enable it to be distinguished from groups of white blood cells in other classes. This means that the hemolytic agent must be carefully selected, and that measurements must be taken while strictly controlling such measurement conditions as temperature. However, since the detection principle from the outset is based on particle size, this would make it impossible to detect the various characteristics possessed by the particles. For example, it would not be possible to detect the state of nuclear shift of the cells.

An advantage of the second conventional apparatus is that many characteristics can be detected from a single particle by reducing the size of the detecting zone, as mentioned above. However, nowhere does the aforementioned literature describe determining the nuclear shift index of white blood cells, which is one characteristic possessed by white blood cells, or a technique for achieving this.

Nuclear shift index rises as the maturity of white blood cell granulocytes progresses. FIG. 12 is a view for describing the nuclear shift of neutrophils cited in "Clinical Laboratory Methods" by Masamitsu Kanai, et al., 28th Edition, Vol. 6, p 50. An increase in neutrophils with a small number of lobes is referred to as "left shift". If an increase in the total number of white blood cells appears at this time, this indicates a highly active myeloid function and the likelihood of leukemia. If a reduction in the total number of white blood cells appears, myeloid function is considered to be impaired and the patient is readily susceptible to infection. An increase in neutrophils with large number of lobes is referred to as "right shift". There is often a decrease in the total number of white blood cells in this case as well. This is considered to indicate pernicious anemia.

Thus, determining the lobe state of specific cellular nuclei in various white blood cells by examination has great clinical significance.

SUMMARY OF THE INVENTION

The apparatus and method of the present invention are intended to meet this demand. Thus, an object of the present invention is to provide an apparatus and method through which an index (shift index) indicating the lobe state of cellular nuclei can be obtained by processing detected particle signals.

The particle analyzing apparatus and method of the invention are based on the following principle: When a particle stream is irradiated with a laser beam narrow in the direction of particle flow and wide in the direction perpendicular to the particle flow, the waveform of the detection signal becomes more complicated the more complex the shape of the particle nucleus. By extracting such characteristics as the degree of complexity of the detection signal waveform, the nuclear shift index of the particle is measured to enable analysis of particles such as white blood cells.

The present invention provides a particle analyzing apparatus for passing a suspension in which particles are suspended, such as a blood specimen, in the form of a sheathed stream, forming a detecting zone by irradiating a zone, in which particles flow substantially in single file in the direction of flow, with a laser beam in a direction perpendicular to the direction of particle flow, and detecting, at one or a plurality of locations, an optical change in scattered light or fluorescent light which is produced by particles passing through the detecting zone one at a time, thereby obtaining one or more types of signals with respect to a single particle; the apparatus characterized by comprising means for projecting the laser beam, so as to be narrower than the diameter of a particle nucleus in the direction of particle flow, and wider than the diameter of the particle in a direction perpendicular to the particle flow; means for obtaining a particle signal by detecting scattered light produced by the particle; first characteristics quantity extracting means for extracting the amount of high-frequency components, which are contained in the particle signal, in order to determine the complexity of the particle nucleus; and second characteristic quantity extracting means for extracting the magnitude of a difference between the particle signal and a signal, obtained by flipping over the particle signal in terms of time, in order to determine the symmetry of the particle nucleus.

The particle analyzing method of the invention is characterized by obtaining a nuclear shift index, which indicates the lobe state of a nucleus, for every particle using particle nucleus complexity data obtained by the first characteristic quantity extracting means, and particle nucleus data obtained by the second characteristic quantity extracting means.

The first characteristic quantity extracting means for extracting particle nucleus complexity can comprise a differentiator for differentiating an inputted particle signal, a rectifier connected to an output side of the differentiator for full-wave rectifying the output signal thereof, an integrator connected to an output side of the rectifier for integrating an output signal thereof, and an A/D converter connected to an output side of the integrator for converting an analog output thereof into digital data.

Further, in order to implement the function of the first characteristic quantity extracting means by digital signal processing, the first characteristic quantity extracting means can comprise an A/D converter for sampling and successively converting the inputted particle signal into digital data at equally spaced clock pulses, memory means connected to an output side of the A/D converter for temporarily storing the digital data, a subtracter connected to the output side of the A/D converter and an output side of the memory means for successively calculating the absolute value of a difference between data, which prevails at the present time, outputted by the A/D converter and data, which prevailed one clock interval earlier than the present time, outputted by the memory means, and an accumulator connected to an output side of the subtracter for successively cumulatively adding data outputted by the subtracter.

The second characteristic quantity extracting means for extracting the symmetry of the particle nucleus can comprise an A/D converter for sampling and successively converting the inputted particle signals into digital data at equally spaced clock pulses, two memory means connected to an output side of the A/D converter for successively storing sampling data indicative of the particle signal while a single particle signal is present, a subtracter connected to an output side of one memory means and to an output side of the other memory means for successively calculating, with regard to a single particle signal, the absolute value of a difference between data successively outputted by the one memory means in a sequence the same as the passage of time, and data successively outputted by the other memory device in a sequence that is the reverse of the passage of time, this calculation being performed after the A/D conversion ends, and an accumulator connected to an output side of the subtracter for successively cumulatively adding data outputted by the subtracter.

In operation, the suspension of blood particles is passed in the form of a sheathed stream and is irradiated with a laser beam the width whereof is smaller than the diameter of the particle nucleus in the direction of particle flow, and larger than the diameter of the particle in the direction perpendicular to the particle flow. By passing the particle through the detecting zone, which is the zone irradiated, scattered light conforming to the structure of the particle nucleus is generated. Accordingly, by detecting this optical change, a particle signal which includes information relating to the structure of the nucleus can be obtained. More specifically, there is a relationship between complexity of cell shape and the complexity of the particle signal waveform. By extracting the amount of components in the high-frequency region contained in the particle signal waveform by the first characteristic quantity extracting means, the complexity of the waveform can be extracted and it is possible to determine the complexity of the particle nucleus in a case where the particle is viewed from a certain side face thereof.

The degree of symmetry of the shape of the nucleus in the particle flow direction can be ascertained by investigating the symmetry of the particle signal waveform. Accordingly, it is possible to distinguish the symmetry of the particle nucleus by obtaining, via the second characteristic quantity extracting means, the magnitude of a difference between the particle signal waveform and a signal waveform which results when the particle signal is flipped over in terms of time.

Further, if the data indicative of the complexity of the nucleus and the data indicative of its symmetry obtained by the first and second characteristic quantity extracting means are used, the nuclear shift index can be calculated without relation to the orientation of the particle when it passes through the detecting zone.

The foregoing operation will now be explained in further detail in conformity with the embodiment of the invention described later.

Referring now to FIG. 2, the particle signal is differentiated by a differentiator 62, whereby the components in the high-frequency region are extracted. Next, the differentiated signal relating to these components in the high-frequency region is full-wave rectified by a rectifier 64, and the output whereof is integrated by an integrator 66 to obtain the area of the waveform of the differentiated signal. In other words, the amount of complexity of the particle signal waveform is delivered to the integrator 66, the analog output of which is converted into digital data by an A/D converter 68 in order to obtain a numerical value. Thus is extracted the amount of components in the high-frequency region contained in the particle signal.

Referring now to FIG. 3, the particle signal is sampled and successively converted into digital data at equally spaced clock pulses by an A/D converter 80. These data are temporarily retained in memory means 82 in successive fashion, and then are outputted sequentially. A subtracter 84 successively calculates the absolute value of the difference between the digitized data, which prevails at the present time, outputted by the A/D converter 80, and the digitized data, which prevailed one clock interval earlier than the present time, outputted by the memory means 82. The absolute value of this difference is successively cumulatively added by an accumulator 86 to obtain a numberical value. Thus is extracted the amount of components in the high-frequency region contained in the particle signal.

The particle signal is sampled by an A/D converter 80 and successively converted into digital data thereby. The sampling data are successively applied to and stored in two memory means 87, 89. At the end of the A/D conversion regarding a single particle signal, the previously stored sampling data indicative of the single particle signal are successively outputted by the memory means 87, in a sequence the same as the passage of time, and the sampling data indicative of the single particle signal are successively outputted by the other memory means 89, in a sequence that is the reverse of the passage of time. The absolute value of the difference between these two items of data is successively calculated and outputted by the subtracter. The absolute value of the aforementioned difference is cumulatively added by the accumulator, thereby obtaining the magnitude of the difference between the particle signal and a signal which results when the particle signal is turned over in terms of time. The magnitude of this difference is related to the nuclear shift index of the particle.

Other features and advantages of the present invention will be apparent from the following description taken in conjunction with the accompanying drawings.

BRIEF DESCRIPTION OF THE DRAWINGS

FIGS. 10 and 11 are diagrams illustrating the relationship between an irradiating laser beam and a signal, in which FIG. 10 shows the relationship between particles and a slit beam and FIG. 11 shows a particle signal obtained by detecting fluorescence;

DESCRIPTION OF THE PREFERRED EMBODIMENTS

Figure 1:
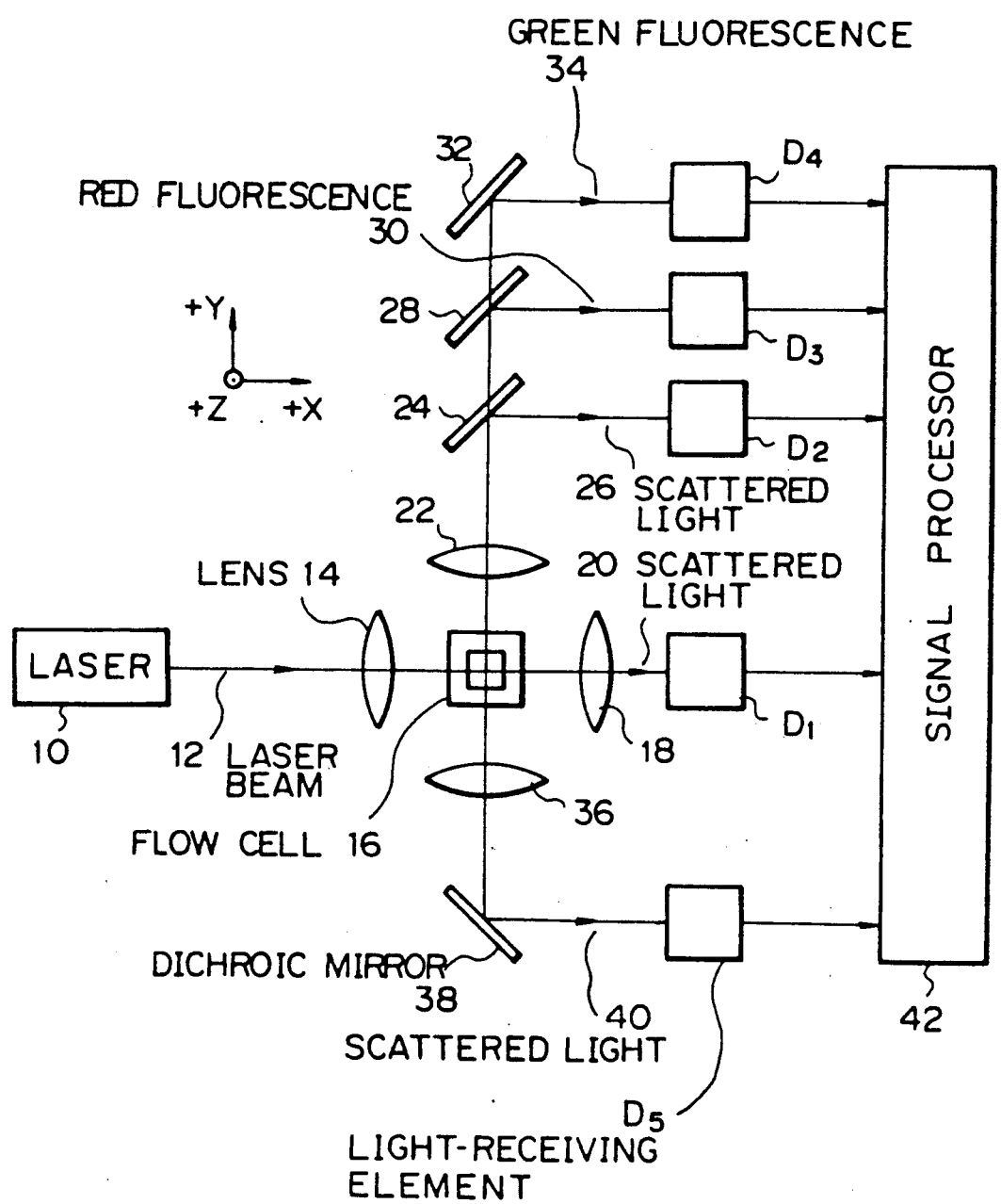
FIG. 1 is a schematic view illustrating an example of an optical system in the particle analyzing apparatus of the present invention.

FIG. 1 is a schematic view illustrating an example of an optical system for obtaining a plurality of types of particle signals with respect to a single particle in a particle analyzing apparatus of the present invention. A laser beam 12, emitted by an argon laser 10 and propagating to the right in FIG. 1 (i.e., along the +X axis), irradiates a specimen of blood or the like which flows through a flow cell 16, in a direction perpendicular to the plane of the drawing (i.e., along the + or −Z axis). The laser beam 12 is condensed by a lens 14, to irradiate the central portion of the flow cell 16, with a beam width reduced along the +Y and −Y axes to the order of 100–150 μm, which is greater than particle diameter, and along the +Z and −Z axes to the order to 2–3 μm, which is less than the diameter of the particle nucleus.

Since it is desired here to measure the characteristics and number of white blood cells, the blood specimen passed through the flow cell 16 should satisfy the following conditions:

(a) Red blood cells, which far outnumber white blood cells, should be destroyed so as not to hamper measurement of the white blood cells.

(b) The treatment used to destroy the red blood cells should not cause a morphological change in the white blood cells (i.e., expansion, contraction, deformation, etc.).

Accordingly, the specimen should be treated by adding to it a first liquid exhibiting acidity (e.g., pH 4.5), and low osmotic pressure (e.g., an osmotic pressure of 50 mOsm/kg), incubating the specimen (for example, at 25° C. for 20 seconds), adding a second liquid exhibiting alkalinity (e.g., pH 9.8–9.9) and high osmotic pressure (e.g., an osmotic pressure of 2200 mOsm/kg), incubating the specimen (for example, at 25° C. for 40 seconds), and returning the specimen to the isotonic state (an isotonic pressure of 286 mOsm/kg). Since red blood cells exhibit little resistive pressure, they are destroyed by the acidic treatment at low osmotic pressure. White blood cells, on the other hand, possess a high resistive pressure and remain in the specimen without being destroyed. If desired, the first liquid may contain a fluorescent dye for staining the nuclei of the white blood cells.

With its periphery enveloped by a fluid sheath, the specimen passes through the central portion of the flow cell 16 in a fine stream. By passing the white blood cells through the detection zone, which is the zone irradiated by the laser beam, one at a time substantially in a single file in the direction of flow, scattered light or fluorescence is emitted in various directions conforming to the structure of each particle nucleus. If the structure of a nucleus is complex, then a complex optical signal will be emitted.

Forward-scattered light 20, namely scattered light emitted in the forward direction (along the $+X$ axis), is partially shielded by a light-shielding plate (condensed by a lens 18), and detected by a photodiode $D_1$. Meanwhile, side-scattered light 26, 30, 34, namely light emitted to one side (along the $+Y$ axis), is condensed by a lens 22. The scattered light 26 is reflected by a dichroic mirror 24, which has the ability to transmit and reflect selected wavelengths, and is detected by a photomultiplier tube $D_2$. Fluorescence 30, 34 passes through the dichroic mirror 24. Red fluorescence 30 is reflected by a dichroic mirror 28 and detected by a photomultiplier tube $D_3$. Green fluorescence 34 is reflected by a dichroic mirror 32, and detected by a photomultiplier tube $D_4$.

Side-scattered light 40 is light emitted to the other side (along the $-Y$ axis), which is a direction symmetrical to the above-mentioned first side direction with respect to the optic axis of the laser. This side-scattered light 40 is condensed by a lens 36, reflected by a dichroic mirror 38 and detected by a photomultiplier tube $D_5$.

Thus, more types of signals are obtained with regard to a single-particle that passes through the detecting zone. The detected particle signals of the plurality of types are delivered to a signal processor 42, in order to be analyzed. In the present embodiment, the forward-scattered light beam 20 along the $+X$ direction, the side-scattered light beam 26 along the $+Y$ axis, and the side-scattered light beam 40 along the $-Y$ axis are detected by the light-receiving elements $D_1$, $D_2$, $D_5$, respectively, whereby three types of particle signal are obtained. In this embodiment, the nuclear shift index of white blood cells is determined, using the side-scattered light beam 26 along the $+Y$ axis. It is of course permissible to employ a particle signal obtained by detecting other scattered light beams.

Ordinarily, a particle signal having a complex waveform is obtained if the shape of the particle nucleus is complex. Accordingly, the complexity of the shape of a nucleus can be found by applying the particle signal to first characteristic quantity extracting means and extracting the complexity of the signal waveform. However, merely detecting scattered light in one direction allows the complexity of the nucleus to be ascertained as seen only from one side face thereof, and using these data alone to determine the shift index of the nucleus would result in measurement error. Accordingly, in order to reduce the error, it has been considered to detect light scattered in a plurality of directions. If there are many locations at which scattered light is detected, this will make it possible to determine the shape of the nucleus more correctly, with greater accuracy being achieved, the greater the number of locations. Cost rises correspondingly, however. Therefore, as the result of much research, the inventor has found that if it is arranged to extract not only the complexity of a signal waveform, but also the degree of symmetry thereof using the particle signal obtained by detected side-scattered light, then measurement accuracy involved in particle analysis is greatly improved without requiring complicated equipment and operation and without greatly increased expenditures. The degree of symmetry of the particle signal waveform can be regarded as being the degree of symmetry of the shape of the particle nucleus in the direction of particle flow. Accordingly, the degree of nuclear symmetry can be ascertained if the difference between the particle signal, and a signal obtained by flipping the particle signal over in terms of time, is calculated by the second characteristic quantity extracting means. It has been clarified that if the aforementioned data relating to the complexity of a nucleus and the data relating to the symmetry of the nucleus are employed, the shape of the nucleus can be suitably determined, irrespective of the orientation of the particle, as it passes through the detecting zone.

Figures 2, 4, 5:
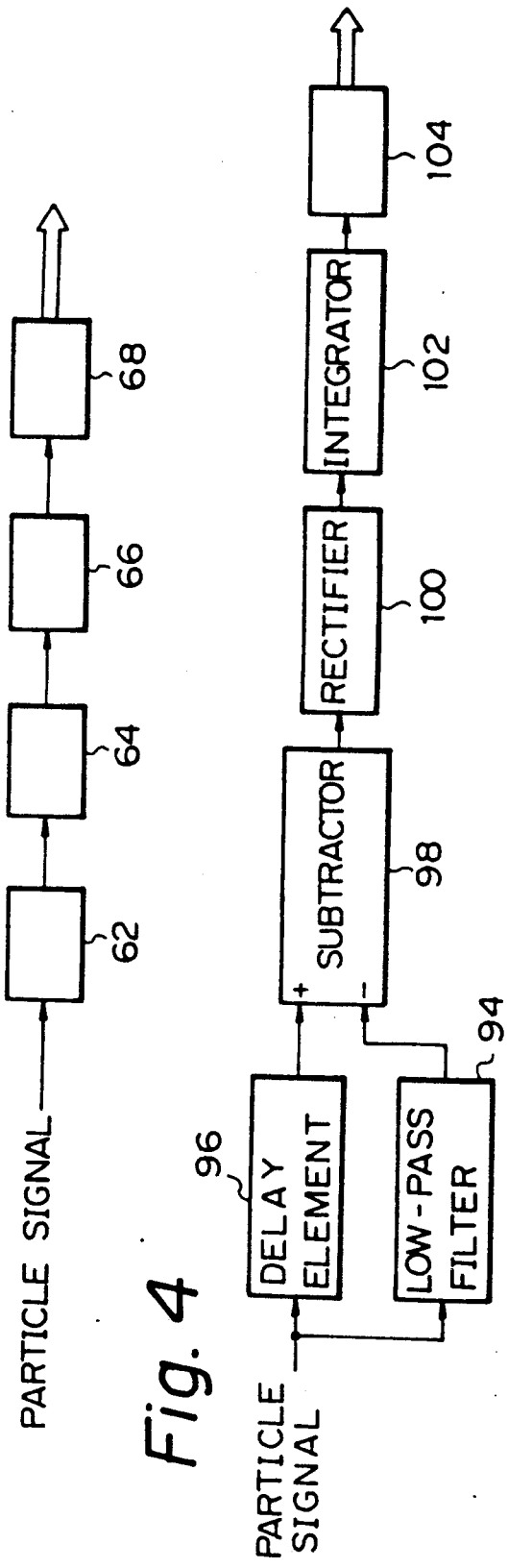
FIG. 2 is a block diagram illustrating an embodiment of first characteristic quantity extracting means.
FIGS. 4 and 5 are block diagrams illustrating other embodiments of the first characteristic quantity extracting means.
Figure 6:
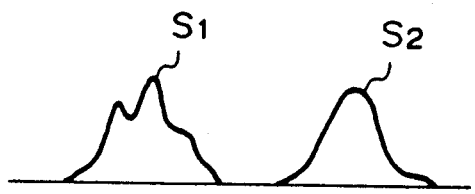
FIGS. 6 and 7 are diagrams respectively illustrating particle signals and signals obtained by differentiating the particles for the purpose of describing the first characteristic quantity extracting means.
Figure 7:
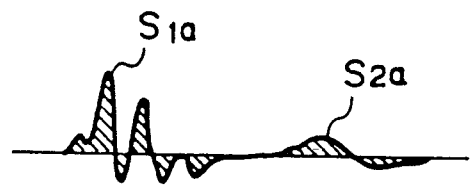

FIG. 2 is a block diagram illustrating an embodiment of first characteristic quantity extracting means for determining the degree of complexity of a nucleus. A particle signal obtained by detecting scattered light along the $+Y$ axis enters a differentiator 62. As shown in FIG. 6, the particle signal of a white blood cell having a nucleus whose lobes have developed has a complex waveform which is very uneven, as shown at $S_1$, while the particle signal of a white blood cell having a nucleus whose lobes have not developed has smooth waveform, as shown at $S_2$. By differentiating these particle signals $S_1$, $S_2$ in the differentiator 62, the components in the high-frequency region of the respective particle signals are emphasized to extract signals $S_1a$, $S_2a$ shown in FIG. 7, respectively. The areas (indicated by the shaded portions) of the differentiated signals $S_1a$, $S_2a$ correspond to the complexities of the particle signals $S_1$, $S_2$, respectively. Accordingly, the differentiated signals $S_1a$, $S_2a$ are full-wave rectified by a rectifier 64 and then integrated by an integrator 66, thereby obtaining an analog signal corresponding to the aforementioned area. This signal is converted into digital data by an A/D converter 80. Thus, the degree of complexity of the waveform of the first particle signal is converted into a numerical value simply and accurately. Thereafter, all circuit elements return to their initial states.

Figure 3:
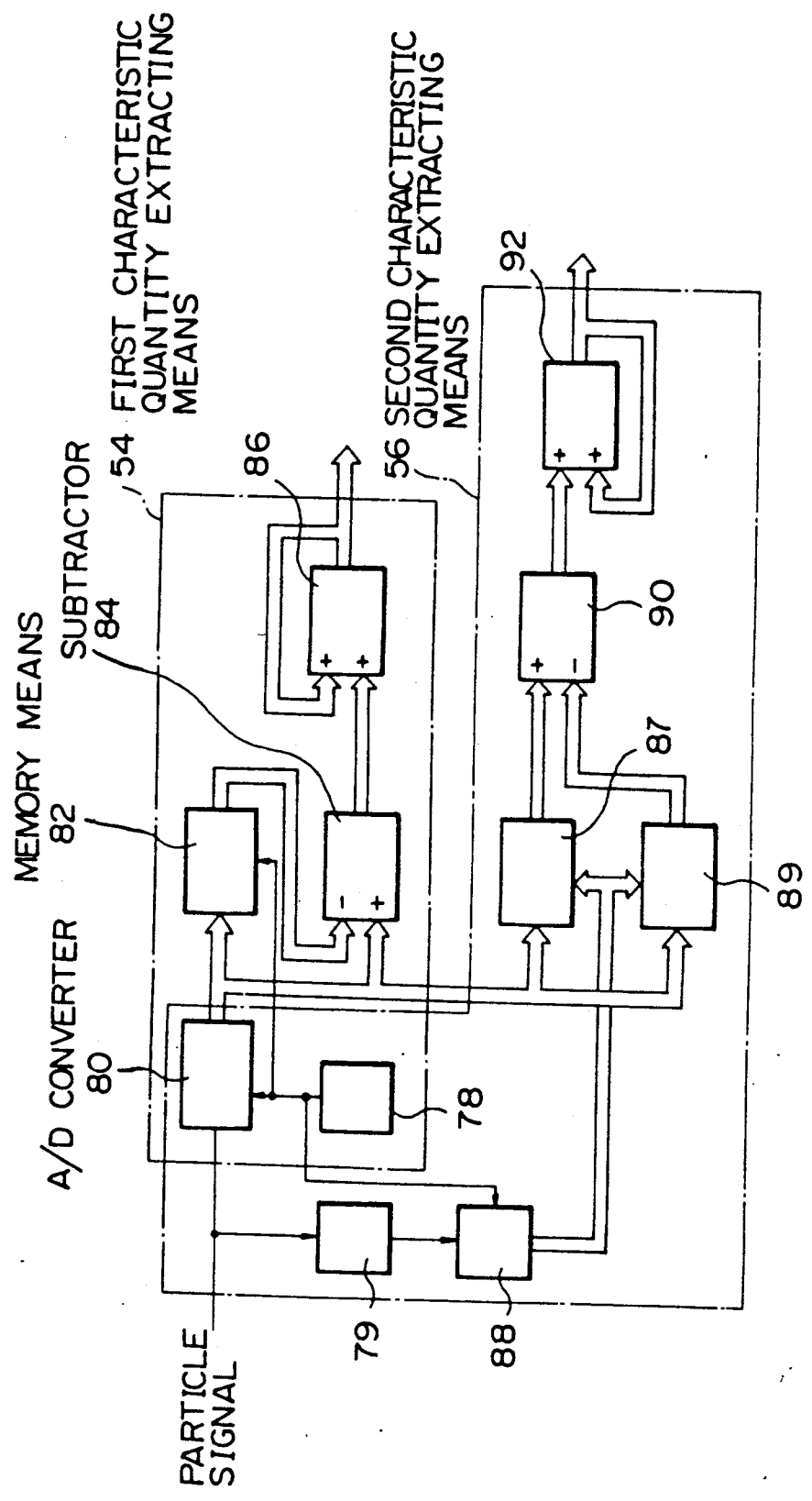
FIG. 3 is a block diagram illustrating an embodiment of characteristic quantity extracting means which jointly employs first characteristic quantity extracting means and second characteristic quantity extracting means.

FIG. 3 is a block diagram illustrating an embodiment of the first and second characteristic quantity extracting means 54, 56, respectively. In FIG. 3, the first characteristic quantity extracting means 54 is adapted to implement the signal processing of FIG. 2 by digital signal processing. The technical concept here is the same as in FIG. 2.

With regard to digital signal processing, a clock generator 78 supplies clock pulses at equal time intervals, at a rate quicker than that at which the particle signal changes. The particle signal enters a high-speed A/D converter 80 and the particle signal is sampled and converted into digital data in response to every clock pulse. The sampling data, indicative of the particle signal, enter a buffer 82 serving as temporary storage means, whereby these data are temporarily preserved and outputted at every clock. Sampling data, which prevail at the present time, outputted by the A/D converter 80 and sampling data, which prevailed one clock interval earlier than the present time, enter a subtracter 84, which outputs the absolute value of the difference between the two items of sampling data. By way of example, the subtracter 84 can be one which performs computation by addition based on complementary numbers. For instance, subtraction processing is performed by re-expressing the sampling data from the buffer 82, as a twos complement and adding the sampling data from the A/D converter 80. The sign of the results of this processing is detected in the form of a sign bit. If the sign is negative, the data is re-expressed as a twos complement and converted into an absolute value. The absolute value of the difference between both items of data, (present-time sampling data and sampling data one time interval earlier than the present time) is thus determined. The data outputted by the subtracter 84 are applied to an accumulator 86 to be cumulatively added thereby. All circuit elements then return to their initial states.

Figure 13:
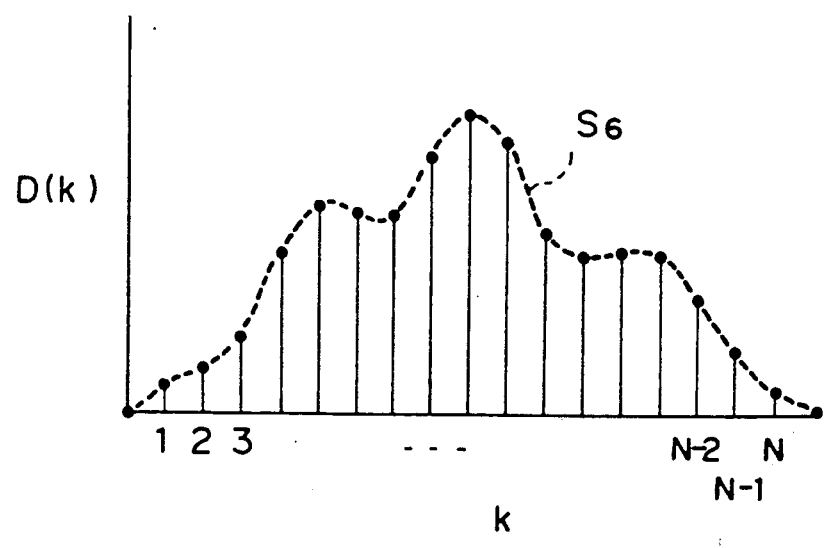
FIG. 13 is a diagram illustrating the sampling of a particle signal.

FIG. 13 is a view for describing the foregoing. A particle signal $S_6$ is sampled and A/D converted every sampling clock, whereby digital data $D(1), D(2), \ldots, D(N)$, indicative of the particle signal are successively obtained. These data are processed by the buffer 82 and subtracter 84, to successively obtain absolute values of the difference between $|D(R)-D(R-1)|$, where $R=1, 2, \ldots, N$.

A cumulative value $$\sum_{R=1}^{N} |D(R) - D(R-1)|$$

is determined by the accumulator 86.

By thus adopting digital signal processing, measurement precision is improved and the system is made less susceptible to noise.

Figure 9:
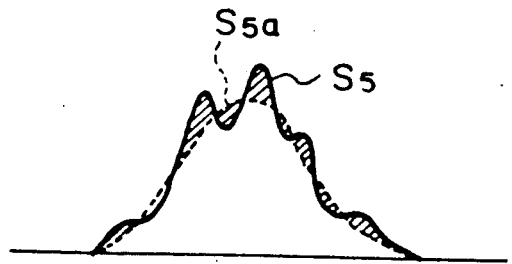
FIG. 9 is a diagram for describing another embodiment of the first characteristic quantity extracting means, this diagram showing a signal obtained by eliminating components in a high-frequency region from the particle signal, as well as the original particle signal.
Figure 10:
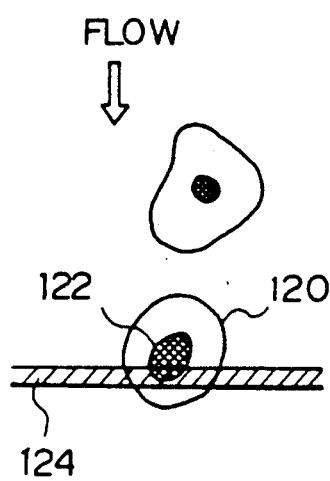
Figure 11:
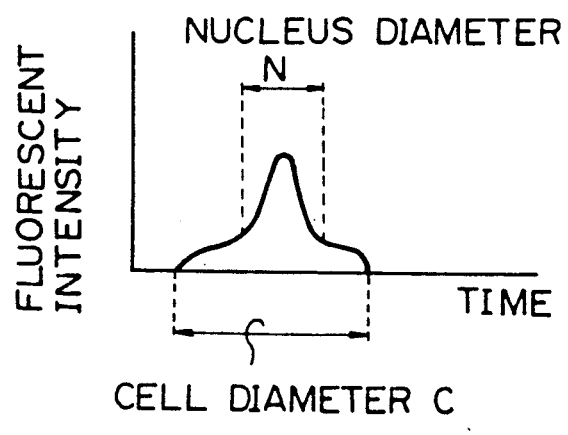
Figure 12:
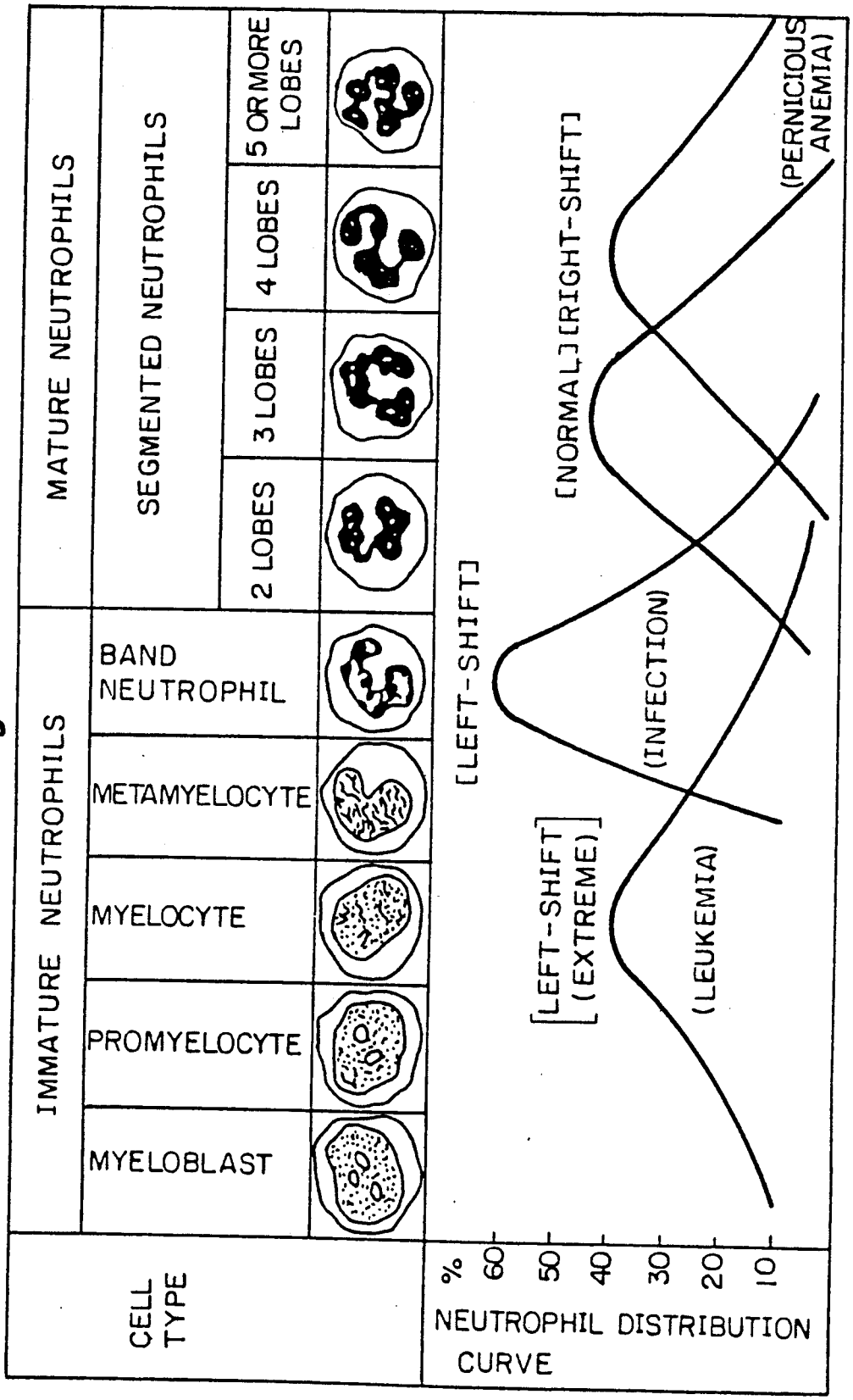
FIG. 12 is a view illustrating the lobes of neutrophil nuclei.

The following approach can also be adapted in order to obtain the complexity of the particle signal waveform as a numerical value: As shown in FIG. 9, signal components in the high-frequency region can be removed from the particle signal $S_5$ by calculating the difference between the particle $S_5$ and the signal $S_{5a}$, which is obtained by eliminating signal components in the high-frequency region from the particle signal $S_5$. The area (the shaded portion) of the difference can be adapted as representing the complexity of the waveform of particle signal $S_5$. The means for accomplishing this will now be described.

FIG. 4 is a block diagram showing another embodiment of the first characteristic quantity extracting means. Here the differentiator 62 in FIG. 2 is replaced by a low-pass filter 94, a delay element 96 and a subtracter 98. The particle signal enters the low-pass filter 94 and the delay element 96. The particle signal applied by the low-pass filter has its high-frequency components removed, whereby ripple is removed from the waveform to obtain a waveform which is smooth. The delay element 96 subjects the particle signal to a phase delay equivalent to that produced by the action of the low-pass filter 94. The original signal and the signal outputted by the low-pass filter 94, which are now in phase, enter the subtracter 98, which calculates the difference between them. The resulting signal is full-wave rectified by a rectifier 100, whose output is integrated by an integrator 102. The integrated output is converted into a digital numerical value by an A/D converter 104.

FIG. 5 is a block diagram illustrating another embodiment of the first characteristic quantity extracting means. Here the function of the first characteristic quantity extracting means shown in FIG. 4 is implemented by digital signal processing. The technical concept is the same as that of the block diagram shown in FIG. 4. The particle signal is sampled and digitized by a high-speed A/D converter 108 in response to every clock pulse issued by a clock generator 106. The digitized particle signal is delivered to a buffer 110 serving as temporary memory means, and the signal data are successively outputted after being temporarily stored in sync with the clock pulses. The digitized particle signal is also delivered to a digital filter 112, the action of which is the same as that of a low-pass filter. The digital filter 112 can be constituted by a multiplier, accumulator and the like, or can be implemented by software. The temporarily stored digital signal and the filtered digital signal are successively delivered to a subtracter 114, which successively calculates the absolute value of the difference between the two signals. The resulting absolute values are accumulated by an accumulator 116.

Figure 8:
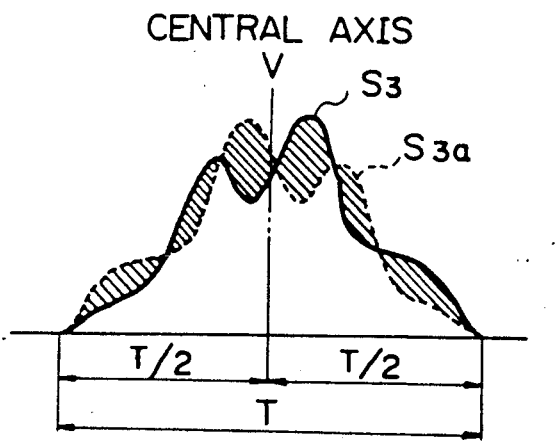
FIG. 8 is a diagram illustrating a particle signal and a signal obtained by flipping over the particle signal for the purpose of describing the second characteristic quantity extracting means.

The second characteristic quantity extracting means for determining the degree of symmetry of a particle nucleus will now be described. A signal $S_{3a}$ shown in FIG. 8 is obtained by flipping a particle signal $S_3$ over, about a central axis V, in terms of time. The central axis V equally divides the duration T of the particle signal $S_3$. The difference between the particle $S_3$ and the signal $S_{3a}$ obtained by flipping over the particle signal $S_3$ corresponds to the area of the shaded portion. Accordingly, the degree of complexity of the nucleus can be determined by extracting this area using the second characteristic quantity extracting means.

In FIG. 3, the data sampled and digitized by the high-speed A/D converter 80 successively enter the memories 87, 89. Meanwhile, the particle signal corresponding to each particle enters a signal discriminator 79, which senses a particle signal that exceeds a threshold value. Even if the threshold value is exceeded, signal width is small in case of simple noise and large if a plurality of particles pass through the detecting zone simultaneously. Therefore, if the width of the particle signal is monitored, the particle signal corresponding to a single particle can be sensed as well as its leading and trailing edges. The detection signal is applied to a memory controller 88, which proceeds to form addresses for extracting the data from memories 87, 89. For example, as shown in FIG. 13, assume that a single particle signal is sampled to successively obtain N items of data $D(1), D(2), \ldots, D(N-1), D(N)$. Here $D(1)$ is an item of data representing the leading edge of the particle signal, and $D(N)$ is an item of data representing the trailing edge of the particle signal. An arbitrary item of data $D(R)$ is stored at an address (R) of each of the memories 87, 89, where $R = 1, 2, \ldots, N$. After N items of sampling data have been stored, i.e., after a single particle signal has been subjected to the A/D conversion, the memory controller 88 designates the addressed of the memories 87, 89 so that the aforementioned data are successively read out of these memories and applied to a subtracter 90. More specifically, address (R) of memory 87 is designated to read out data (R), and address $(N-R+1)$ of memory 89 is designated to read out data $D(N-R+1)$. The extracted items of data $D(R), D(N-R+1)$ are fed into the subtracter 90, which proceeds to calculate the absolute value $|D(R), D(N-R+1)|$ between these two items of data. The absolute value is applied to the accumulator 92. The foregoing processing is in regular order from 1 to N with regard to R = 1, 2, ..., N. As a consequence, the accumulator 92 obtains the result $$\sum_{R=1}^{N} |D(R) - D(N - R + 1)|.$$

This value accurately represents the area of the shaded portion shown in FIG. 8. In other words, the degree of symmetry of the particle signal is thus converted into a numerical value in simple and ready fashion. Since signal processing is executed digitally, measurement precision is excellent and not readily susceptible to noise. Following the above processing, each circuit element returns to its initial state.

It is possible to adopt an arrangement in which an additional set of memories is provided in parallel with the set of memories 87, 89 (for a total of four memories), the particle sampling data already stored are successively extracted from the one set of memories 87, 89, processing for obtaining the absolute value of the difference between the data and for cumulatively adding the absolute values is executed and, if the next particle signal arrives in the midst of this processing, the sampling data indicative of this particle signal are stored in the other set of memories. By adopting this arrangement, even particle signals that are very close together can be processed without being missed.

Thus, a lobe index B indicating the lobe state of every single white blood cell is defined and determined, by arithmetic operations, using data F indicating the complexity of a particle nucleus and data T indicating the symmetry of the particle nucleus, these data F, T being quantified upon extraction from the particle signal. For example, B can be determined as follows:

$$B = K(F + T) + C, \text{ or}$$

$$B = K\sqrt{F^2 + T^2} + C.$$

Here K and C are constants.

Thus, an index is obtained that indicates the lobe degree of individual particles. Since other means can be employed to individually determine, say, the peak values of particle signals, a demarcation line can be drawn on a distribution in which peak value is plotted along the horizontal axis and frequency along the vertical axis, thus enabling neutrophils to be distinguished from other white blood cells. This makes it possible to provide valuable clinical information, such as a lobe index distribution and mean lobe index regarding particles identified as being neutrophils.

When the optical system of FIG. 1 is used, the apparatus can be arranged to detect fluorescence of different wavelengths using a dye which stains each white blood cell in conformity with the type thereof. Each white blood cell can be classified by respectively determining the peak values or area values of the different types of particle signals, obtaining a two-dimensional distribution in which fluorescents of different wavelengths or fluorescent and the above-mentioned scattered light are taken as the axes, and providing a demarcation line on the distribution.

By making overall use of the nuclear shift indices of individual particles obtained by the particle analyzing apparatus and method of the present invention, the particles can be classified and counted more precisely. This can be effectively exploited in accurately detecting and assessing abnormal particles.

In accordance with the particle analyzing technique of the present invention as described above, a particle is irradiated with a laser beam formed to be narrower than the diameter of the particle nucleus in the direction of particle flow and wider than the diameter of the particle in a direction perpendicular to the particle flow, and side-scattered light beams emitted by the particle is detected and utilized as a particle signal. This makes it possible to obtain information that better reflects the structure of the nucleus within the particle. Also, nuclear complexity and symmetry useful in obtaining nuclear shift index are determined by first and second characteristic quantity extracting means, respectively. In accordance with the present invention, the data indicative of nuclear complexity and symmetry are used to accurately determine, for individual particles, an index (shift index) which well expresses the lobe state of the particle nucleus. This can be accomplished through simple calculation and without relation to the orientation of particles undergoing analysis in the particle flow. By making comprehensive use of the index, a particle measurement technique can be realized that is extremely valuable in terms of clinical examination.

The first characteristic quantity extracting means in claim 2 of the claims is simple in construction and accurately determines the complexity of a particle nucleus. In accordance with claim 3, the first characteristic quantity extracting means is such that the means of claim 2 is implemented digitally. It also serves to improve measurement precision and make the apparatus less susceptible to noise.

The second characteristic quantity extracting means in claim 4 of the claims is simple in construction and accurately determines the symmetry of a particle nucleus. It also serves to improve measurement precision and make the apparatus much less susceptible to noise.

As many apparently widely different embodiments of the present invention can be made without departing from the spirit and scope thereof, it is to be understood that the invention is not limited to the specific embodiments thereof except as defined in the appended claims.

What is claimed is:

1. A particle analyzing apparatus for determining a nuclear shift index of a particle, the apparatus forming a detecting zone by irradiating a zone, in which particles flow substantially in single file, with a laser beam in a direction perpendicular to the direction of particle flow, and detecting at one or a plurality of locations, an optical change produced in the detecting zone when particles pass through the detecting zone one at a time, thereby obtaining one or plural types of signals with respect to a single particle, said apparatus comprising:

a laser beam irradiating zone for performing irradiation with said laser beam formed to be narrower than a diameter of a particle nucleus in the direction of particle flow and wider than the diameter of the particle nucleus in a direction perpendicular to the particle flow, and detecting scattered light emitted by the particle nucleus, thereby obtaining a particle signal;

first characteristic quantity extracting means for extracting high-frequency components contained in the particle signal, in order to determine a degree of complexity of the particle nucleus;

second characteristic quantity extracting means for extracting a magnitude of a difference between the particle signal and a signal obtained by flipping over said particle signal in terms of time, in order to determine a degree of symmetry of said particle nucleus; and means for determining the nuclear shift index from said first and said second characteristic quantity extracting means.

2. The apparatus according to claim 1, wherein said first characteristic quantity extracting means comprises:
a differentiator for differentiating said particle signal;
a rectifier connected to an output side of said differentiator for full-wave rectifying an output signal thereof;
an integrator connected to an output side of said rectifier for integrating an output signal thereof; and
an A/D converter connected to an output side of said integrator for converting an analog output thereof into digital data.

3. The apparatus according to claim 1, wherein said first characteristic quantity extracting means comprises:
an A/D converter for sampling and successively converting the particle signal into digital data at equally spaced clock pulses;
clock means coupled to said A/D converter for producing equally spaced clock pulses;
memory means connected to an output side of said A/D converter for temporarily storing the digital data;
a subtracter connected to the output side of said A/D converter and an output side of said memory means for successively calculating an absolute value of a difference between data, which prevails at a particular time, outputted by said A/D converter and data, which prevailed one clock interval earlier than the particular time, outputted by said memory means; and
an accumulator connected to an output side of said subtracter for successively cumulatively adding output value data outputted by said subtracter.

4. The apparatus according to any one of claims 1 to 3, wherein said second characteristic quantity extracting means comprises:
an A/D converter for sampling and successively converting said particle signal into digital data at equally spaced clock pulses;
clock means coupled to said A/D converter of said second characteristic quantity extracting means for producing equally spaced clock pulses;
two memory means connected to an output side of said A/D converter for successively storing sampling data indicative of the particle signal while a single particle signal is present;
a subtracter connected to an output side of one memory means and to an output side of the other memory means for successively calculating, with regard to a single particle signal, an absolute value of a difference between data successively outputted by said one memory means in a sequence the same as the passage of time and data successively outputted by said other memory means in a sequence the same as the passage of time and data successively outputted by said other memory means in a sequence that is the reverse of the passage of time, said calculation being performed after the A/D conversion ends; and
an accumulator connected to an output side of said subtracter for successively cumulatively adding data outputted by said subtracter.

5. In a particle analyzing apparatus for forming a detecting zone by irradiating a zone, in which particles flow substantially in single file, with a laser beam in a direction perpendicular to a direction of particle flow, and detecting, at one or a plurality of locations, an optical change produced in the detecting zone when particles pass through the detecting zone one at a time, thereby obtaining one or plural types of signals with respect to a single particle, a particle analyzing method for determining a nuclear shift index of a particle, comprising the steps of:
performing irradiation with a laser beam formed to be narrower than a diameter of a particle nucleus in the direction of particle flow and wider than the diameter of the particle nucleus in a direction perpendicular to the particle flow, and detecting a particle signal resulting from scattered light emitted by the particle nucleus;
extracting high-frequency components contained in the particle signal, in order to determine a degree of complexity of the particle nucleus;
extracting a magnitude of a difference between the particle signal and a signal, obtained by flipping over said particle signal in terms of time, in order to determine a degree of symmetry of the particle nucleus; and
determining the nuclear shift index from said degree of complexity and said degree of symmetry of the particle nucleus.

* * * * *

UNITED STATES PATENT AND TRADEMARK OFFICE
CERTIFICATE OF CORRECTION

PATENT NO. : 5,047,963
DATED : September 10, 1991
INVENTOR(S) : Kosaka

It is certified that error appears in the above-identified patent and that said Letters Patent is hereby corrected as shown below:

```
     Column 5, lines 17-18, change "Thus is extracted the amount
of" to --Thus, the--.
     Column 5, line 19, after "signal" insert --are extracted--.
     Column 5, line 32, change "numberical" to --numerical--.
     Column 5, lines 32-33, change "Thus is extracted the amount
of" to --Thus, the--.
     Column 5, line 34, after "signal" insert --are extracted--.
     Column 9, line 8, after "complement" insert --,-- (comma).
     Column 9, line 23, after "signal" insert --,-- (comma).
     Column 12, line 9, after "particle" change "is" to --are--.
```

Signed and Sealed this

Sixteenth Day of March, 1993

Attest:

STEPHEN G. KUNIN

Attesting Officer  Acting Commissioner of Patents and Trademarks